US005783555A

United States Patent [19]

Suzuki et al.

[11] Patent Number: 5,783,555
[45] Date of Patent: Jul. 21, 1998

[54] ULINASTATIN-CONTAINING SUPPOSITORY

[75] Inventors: Shigeharu Suzuki; Katsumi Takaada, both of Tokyo, Japan

[73] Assignee: Mochida Pharmaceutical Co., Ltd., Tokyo, Japan

[21] Appl. No.: 605,202

[22] PCT Filed: Dec. 28, 1995

[86] PCT No.: PCT/JP95/02762

§ 371 Date: Aug. 29, 1996

§ 102(e) Date: Aug. 29, 1996

[87] PCT Pub. No.: WO96/20726

PCT Pub. Date: Jul. 11, 1996

[30] Foreign Application Priority Data

Dec. 29, 1994 [JP] Japan ................................. 6-338313

[51] Int. Cl.$^6$ ................................................ A61K 38/22
[52] U.S. Cl. ........................ 514/2; 514/21; 424/545; 424/436
[58] Field of Search ...................... 514/2, 21; 424/545, 424/436

[56] References Cited

U.S. PATENT DOCUMENTS

| 4,368,185 | 1/1983 | Mizuno et al. ............ 424/436 |
| 4,871,777 | 10/1989 | Breitzke . |
| 5,489,577 | 2/1996 | Ikeda et al. ............. 424/436 |
| 5,504,065 | 4/1996 | Hattori et al. . |

FOREIGN PATENT DOCUMENTS

| 03 32222A2 | 9/1989 | European Pat. Off. . |
| 1097083 | 8/1993 | Germany . |
| 55-81812 | 6/1980 | Japan . |
| 57131727 | 8/1982 | Japan . |
| 63-255216 | 10/1988 | Japan . |
| 1-294632 | 11/1989 | Japan . |
| 2 145527 | 6/1990 | Japan . |
| 5 58910 | 3/1993 | Japan . |
| 6 135852 | 5/1994 | Japan . |
| 95 12406 | 5/1995 | WIPO . |

OTHER PUBLICATIONS

Patent Abstracts of Japan, vol. 012, No. 059 (C–478), 23 Feb. 1988 & JP 62 205033 A (Osamu Matsuo), 9 Sep. 1987, (Abstract).

Database WPI, Week 8108, Derwent Publications Ltd., London, GB; AN–12561D (08) XP002033327 (Abstract) & JP 55 160 724 A (Mochida Pharm. Co. Ltd.) 13 Dec. 1980 (Abstract).

Kanayama et al., (1992), Acta Obst Gynaec Jpn vol. 44, No. 4, pp.477–482.

Kanayama (1994), Acta Obst Gynaec Jpn vol. 46, No. 8, pp.673–685.

*Primary Examiner*—Jean C. Witz
*Attorney, Agent, or Firm*—Birch, Stewart, Kolasch & Birch, LLP

[57] ABSTRACT

Ulinastatin-containing suppository is produced by emulsifying an aqueous solution of ulinastatin in an oily base uniformly in the presence of an emulsifier and then solidifying the emulsion.

The ulinastatin-containing suppository exhibits high stability even if it is stored for a prolonged time. In addition, it can be manufactured on an industrial scale.

4 Claims, No Drawings

ULINASTATIN-CONTAINING SUPPOSITORY

TECHNICAL FIELD

This invention relates to a suppository that contains ulinastatin as an active ingredient and which has an aqueous solution of ulinastatin emulsified in an oily base uniformly to provide a safe and stabilized formulation. More particularly, the invention relates to a ulinastatin-containing vaginal suppository and a process for its production.

BACKGROUND ART

Ulinastatin is a trypsin inhibitor derived from human urine (hereinafter abbreviated as "HUTI") and it is a glycoprotein having a molecular weight of about 67,000 as isolated and purified from human urine (Proksch et al.: Journal of Laboratory and Clinical Medicine, Vol. 79, p. 491, 1972).

The HUTI has an inhibitory activity on many enzymes such as trypsin, α-chymotrypsin, hyaluronidase, granulocyte elastase and plasmin and clinically it has been found to be effective and safe in the treatment of acute pancreatitis, acute failures in circulatory organs, etc. (Kosuzume et al.: IGAKU NO AYUMI, Vol. 125, pp. 187–190, 1983; Honjo et al.: IGAKU NO AYUMI, Vol. 129, pp. 70–83, 1984; Yamamura et al.: IGAKU NO AYUMI, Vol. 129, pp. 730–738, 1984). For its indications, HUTI was first formulated as a pharmaceutical drug by Mochida Pharmaceutical Co., Ltd. and put on the market in 1985 under the trade name "MIRACLID".

It has recently been reported that administration of ulinastatin into the vagina is effective for the treatment of threatened premature delivery and the following methods are known: ulinastatin is absorbed by a tampon, which is subsequently retained within the cervix (SHUSANKI IGAKU, Vol. 21, No. 1, pp. 57–60, 1991); the vagina is irrigated daily with physiological saline containing ulinastatin (NIHON SANFUJINKA SHINSEIJI KETSUEKI GAKKAISHI, Vol. 2, No. 1, pp. 107–110, 1992); ulinastatin is formulated as a vaginal suppository (Acta Obst. Gynaec. Jpn., Vol. 44, No. 4, pp. 477–482, 1992).

The last mentioned document discloses a ulinastatin suppository having a freeze-dried powder of ulinastatin dispersed in hard fat [Witepsol W35 (Mitsuba Co., Ltd.)]; however, it has no disclosure at all about the stability of ulinastatin.

The ulinastatin-containing suppository is also disclosed in other documents, i.e., Unexamined Published Japanese Patent Application (kokai) Hei 2-145527 which teaches its use as an AIDS treating and inhibiting agent, and Unexamined Published Japanese Patent Application Sho 55-160724 which teaches its use as an anti-shock agent; however, these documents make no description of specific formulae for the suppository.

The only formula for suppository that is specifically set forth in the above-mentioned documents has several problems such as that the preliminary step of freeze-drying ulinastatin is needed and that freeze-dried powder having such a property that it will not be readily dispersed uniformly in oily bases, and even if it is dispersed, the particles tend to reaggregate and sediment. The reaggregation cannot be avoided by using gelatin as a stabilizer and substituting a base of low hydroxyl value which is known to stabilize drugs is by no means effective. Therefore, the methods mentioned above present difficulty in assuring the stability of ulinastatin in the suppository during prolonged storage and it would be difficult to realize industrial-scale production of suppositories containing ulinastatin at uniform concentration.

There are very few technologies available for incorporating proteins into oily bases with the aid of emulsifiers and no disclosure has been made of achieving stabilization within oily bases. For example, Unexamined Published Japanese Patent Application Sho 55-81812 discloses a suppository for the treatment of diabetes that has an islet-activating protein dispersed in fat-type or water-miscible bases with the aid of a nonionic and/or anionic surfactant but no mention is made of the stability of the protein. Japanese Unexamined Published Japanese Patent Application Sho 63-255216 discloses a suppository base composition exhibiting an excellent emulsifying action on water, an aqueous solution of an active ingredient and a polar active ingredient but again no mention is made of the stabilization of proteins. Unexamined Published Japanese Patent Application Hei 1-294632 discloses a highly stable, physiologically active polypeptide containing agent for transvaginal administration but the disclosure only concerns the fact that calcitonin and insulin which have lower molecular weights than ulinastatin are stable within the transvaginal agent during prolonged storage or at the site of administration.

It is generally important with suppositories that the stability of the drug be maintained during storage by insuring that the respective components of the suppository will not experience chemical or physical changes or that the proteins will not be decomposed, denatured, aggregated or reduced activity during storage. Other important requirements that should be met by suppositories are: they should melt rapidly at body temperature within body cavities but they should neither become soft in summer nor harden in winter nor should they absorb moisture from the ambient air; they should withstand prolonged storage without causing putrefaction, deterioration, discoloration, mold growth or the denaturing of proteinaceous additives such as natural gelatin; they should permit rapid release of the drug; they should not contain mucosa irritating substances known to be typified by macrogols as water-soluble bases, thus being free of local irritant; and they should present comfortable feel during use as exemplified by the absence of tackiness.

Important considerations in the manufacturing process of suppositories are that they should have the drug dispersed uniformly in the base, have good emulsion stability, can be manufactured straightforwardly and can be produced even at an industrial scale.

Furthermore, pharmaceutical formulation design must be performed with full consideration as to whether the suppository of interest is intended for systemic or local action or whether the site of administration is at the recutum or vagina. For instance, if the site of administration is at the recutum, the ease of absorption of the drug is a dominant factor and if the site is at the vagina, considering such factors as the possible effect on the fetus and the feel of use which depends on the possibility of the base of remaining in the vagina will prove helpful to the provision of easy-to-use suppositories.

However, no ulinastatin-containing suppositories have been disclosed in the prior art that solve the aforementioned problems.

On the other hand, many technologies for stabilizing the ulinastatin-containing composition have been known as shown below. For example, Unexamined Published Japanese Patent Application Hei 6-135852 teaches that by mixing ulinastatin with at least one compound selected from among sodium chloride and potassium chloride and at least one compound selected from among glucose, maltose, xylitol, D-sorbitol, D-mannitol, L-aspartic acid, L-glutamic acid, L-arginine, L-lysine and L-histidine and by then adjusting the pH of the mixture to be within the range of 3.5–5.5, one can prepare an injection that is capable of satisfactory maintenance of long-term stability at room temperature.

Additionally, Unexamined Published Japanese Patent Application Hei 5-58910 teaches that by mixing a freeze-dried preparation containing a trypsin inhibitor with a stabilizer selected from among sucrose, arginine, lysine, glutamic acid and aspartic acid, one can produce a freeze-dried preparation that is highly stable during freeze-drying and storage and which is yet highly soluble during re-dissolution.

However, those patents make no disclosure about the storage stability of ulinastatin that has been emulsified in oily bases with the aid of emulsifiers.

DISCLOSURE OF THE INVENTION

Because of the need for the step of freeze-drying an aqueous solution of ulinastatin, the prior art method which involves dispersing the freeze-dried powder in oily bases has difficulty in producing suppositories of uniform composition, thus making it difficult to manufacture ulinastatin-containing suppositories on an industrial scale. Additionally, the suppositories thus produced are not preferred in terms of the stability of ulinastatin during prolonged storage.

Under these circumstances, the present inventors conducted intensitive studies and found that by adding a stabilizer to the aqueous solution of ulinastatin and formulating a suppository in emulsion with the aid of an emulsifier, the ulinastatin in an oily base could be stabilized over prolonged storage and they also found that formulating an emulsion facilitated the production of suppositories of uniform composition, thereby enabling the manufacture of ulinastatin-containing suppositories on an industrial scale. The present invention has been accomplished on the basis of these findings.

Thus, according to its first aspect, the present invention provides a ulinastatin-containing suppository composition comprising an aqueous solution of ulinastatin emulsified in an oily base.

According to its second aspect, the present invention provides a ulinastatin-containing suppository which is produced by emulsifying an optionally stabilizer-containing aqueous solution of ulinastatin in an oily base uniformly in the presence of an emulsifier and then solidifying the emulsion.

The emulsifier in the above-mentioned ulinastatin-containing suppository is preferably at least one member selected from among sucrose fatty acid esters, glycerol, polyoxyethylene polyoxypropylene glycols and polyoxyethylene hydrogenated castor oil, with sucrose fatty acid esters or polyoxyethylene hydrogenated castor oil being more preferred. The oily base is preferably a hard fat. Additionally, the stabilizer is preferably arginine hydrochloride and/or gelatin.

Further, according to its third aspect, the present invention provides a ulinastatin-containing suppository characterized in that the site of administration is within the vagina.

According to its fourth aspect, the present invention provides a process for producing a ulinastatin-containing suppository characterized by emulsifying an aqueous solution of ulinastatin in an oily base uniformly with the aid of an emulsifier and then solidifying the emulsion.

According to its fifth aspect, the present invention provides a process for producing a ulinastatin-containing suppository characterized by emulsifying a stabilizer- supplemented aqueous solution of ulinastatin in an oily base uniformly with the aid of an emulsifier and then solidifying the emulsion.

In the processes outlined above, an oily base, an emulsifier, an antiseptic and other oleophilic additives are weighed, heated at 50°–80° C. to melt, mixed uniformly and, thereafter, the oil-phase component is held at a temperature suitable for emulsification. In a separate step, an aqueous solution of ulinastatin is diluted with purified water to the necessary concentration and mixed with an isotonic agent, followed by the addition of a stabilizer and any other water-soluble additives, and heating is performed if necessary to make a uniform solution, followed by holding the aqueous-phase component at a temperature suitable for emulsification. Both the oil-phase and aqueous-phase components are charged into an emulsifying vessel held at a temperature suitable for emulsification, emulsified with a homomixer, applied in appropriate amounts into suppository containers, and cooled to solidify, yielding uniform suppositories. Depending on their physicochemical property (solubility), the additives mentioned above may be added to appropriately selected oil-phase or aqueous-phase component. The temperature suitable for emulsification is preferably 35°–600° C., more preferably 35°–45° C.

The present invention relates to both a suppository composition and a suppository prepared by solidifying the composition to a shape. Stated more specifically, the invention provides a suppository composition prepared by the process described above, as well as a uniform oily suppository having a melting temperature of 34°–37° C. that is produced by filling a suppository container with the composition and thereafter solidifying it at room temperature to a shape, with the suppository being removed from the container for use. When administered, the suppository melts at body temperature to release ulinastatin. Unless otherwise noted, the term "suppository of the invention" as used hereinafter shall include the suppository composition too, but not the container.

BEST MODE FOR CARRYING OUT THE INVENTION

The present invention will now be described below in detail.

The ulinastatin-containing suppository of the invention contains not only the drug ulinastatin but also the oily base, emulsifier and optional stabilizer as the essential components and may further contain an antiseptic, an isotonic agent, any other additives, purified water or physiological saline, etc.

Essential combination of components other than ulinastatin include the combination of the oily base, emulsifier, stabilizer, antiseptic and other components, as well as the combination of the oleaginous base, emulsifier, antiseptic and other components.

The ulinastatin to be used in the invention is HUTI and may be purified from human urine by, for example, the method of Sumi et al. (journal of Biochemistry, Vol. 83, pp. 141–147, 1978).

Stated more specifically, human urine is concentrated by a suitable method and passed through an arginine-Sepharose column, with the column-adsorbed component being eluted with 2% aqueous ammonia containing 0.2M sodium chloride. Subsequently, the eluant is loaded on a Sephadex G-100 column to perform gel chromatography in the usual manner, thereby yielding a ulinastatin fraction. The thus purified ulinastatin is an acidic protein with a molecular weight of about 67,000 and an isoelectric point (pI) of 2–3 and which contains 5–12% of a neutral sugar.

It should be noted that the process for producing the ulinastatin which is to be used in the invention is by no means limited to the above-described method.

Moreover, HUTI was first formulated as a pharmaceutical preparation by Mochida Pharmaceutical Co., Ltd. and put on the market in 1985 under the trade name of MIRACLID. The commercially available HUTI (ulinastatin) can also be used in the invention.

The oily base to be used in the invention is selected from among oils and fats such as hard fat and cocoa butter. In fact, however, natural oils and fats have such high iodine values that they are highly prone to putrefy; in addition, their complex polymorphism presents difficulty in controlling the physical properties of the natural oils and fats; therefore, hard fat which is a semi-synthetic triglyceride suits practical purposes.

The hard fat is a semi-synthetic oleaginous base chiefly composed of a triglyceride of saturated fatty acids. The hard fat is generally obtained by hydrolyzing coconut oil, palm kernel oil, etc., adjusting the length of the carbon chain in the obtained fatty acid or hydrogenating the same to yield the desired glycerin ester of the fatty acid. The thus obtained glycerin ester of fatty acids has the fatty acids with carbon chain length of 6–30 and it is primarily an ester with glycerol which is triglyceride, occasionally containing small amounts of unsaturated bonds or mono- and di-glycerides.

The physical properties of the hard fat can be suitably changed by altering the degree of esterification, carbon chain length, the number of unsaturated bonds, etc. or by adding a suitable additive. The physicochemical properties of the hard fat are specified by factors such as melting point, acid value, saponification value, hydroxyl value, unsaponified product (%) and iodine value. In Japan, the entry of "hard fat" appeared in 1984 in the Specifications of Pharmaceutical Components Not Covered by The Pharmacopeia of Japan. In other countries, the hard fat has its quality specified under the names of Adeps Solidus (West Germany and Norway), Massa Esterinca (Portugese) and Adeps Neutrical (Austria) and it is commonly known in the field concerned.

Examples of the hard fat that can be used in the present invention include Witepsol™ (product of Huls AG) and Pharmazol™ (product of Nippon Oil & Fats Co., Ltd.), with Witepsol™, etc. being preferred.

The content of the oily base in the suppository of the invention is preferably 99.5–70 wt %, more preferably 97–75 wt %, of the total quantity of the ulinastatin-containing suppository of the invention, with 90–85 wt % being particularly preferred.

The emulsifier to be used in the invention is selected from among the surfactants described below. Exemplary nonionic surfactants include sorbitan fatty acid esters, glycerol fatty acid esters, glycerol (covering the glycerin and conc. glycerin listed in the Pharmacopeia of Japan), decaglycerin fatty acid esters, polyglycerin fatty acid esters, propylene glycol fatty acid esters, pentaerythritol fatty acid esters, polyoxyethylene sorbitan fatty acid esters, polyoxyethylene sorbitol fatty acid esters, polyoxyethylene glycerin fatty acid esters, polyethylene glycol fatty acid esters, sucrose fatty acid esters, polyoxyethylene alkyl ethers, polyoxyethylene phytosterols, polyoxyethylene phytostanols, polyoxyethylene polyoxypropylene glycol, polyoxyethylene castor oil, polyoxyethylene hydrogenated castor oil, polyoxyethylene lanolin, polyoxyethylene lanolin alcohol, beeswax derivatives, polyoxyethylene alkylamines and polyoxyethylene fatty acid amides.

Exemplary anionic surfactants include alkyl sulfates, polyoxyethylene alkyl ether sulfates, N-acylamino acid or salts thereof, and polyoxyethylene alkyl ether phosphates. Exemplary cationic surfactants include alkyl ammonium salts and alkylbenzyl ammonium salts. Exemplary amphoteric surfactants include betaine acetate and lecithin.

The ulinastatin-containing suppository of the invention is produced by W/O type emulsification such as to have the aqueous-phase component emulsified in the oleaginous base and, hence, an emulsifier having high affinity for the hard fat is preferred. It is also preferred to use an emulsifier that allows the aqueous-phase component to be emulsified stably within the hard fat having high practical value for use with suppositories and which, after solidifying, either retains a high hardness enough to withstand use as suppository or assures uniform and satisfactory properties as a pharmaceutical preparation. Stable emulsification may be evidenced by, for example, the small diameter of the particles in the emulsion, as well as the absence of separation of the aqueous phase, aggregation and sedimentation in the emulsified state during melting or filling into suppository containers. Such stability in emulsification and shaping property upon solidification need be fully taken into account when selecting a suitable emulsifier. Emulsifiers may be used either alone or in combination with themselves. If two or more emulsifiers are to be combined, they may be mixed at any desired proportions.

From practical viewpoints, i.e., low irritation upon use as a pharmaceutical, the ability to guarantee stable emulsification during manufacture and the added advantage of good shaping upon solidification, it is preferred to use at least one emulsifier selected from the group consisting of sucrose fatty acid esters, glycerol, polyoxyethylene polyoxypropylene glycol and polyoxyethylene hydrogenated castor oil.

Sucrose fatty acid esters which are generally referred to as sugar esters are monoesters, diesters, triesters constituted of sucrose and one or more fatty acids or mixtures thereof. Examples of the fatty acid bound to sugar to form sugar esters include stearic acid, palmitic acid, oleic acid and lauric acid. Sugar esters are employed as food additives and the like, particularly as highly safe surfactants.

The sucrose fatty acid esters to be used in the invention are preferably in a powder, liquid or paste form and specific examples are DK Ester™ (product of Daiichi Kogyo K.K.) and Ryoto Sugar Ester™ [product of Mitsubishi Kagaku Foods Co., Ltd. as exemplified by S-170 (sugar stearate ester)].

Examples of the polyoxyethylene polyoxypropylene glycols to be used in the invention include Pluronic™ [product of Asahi Kaden Freund Sangyo K.K., as exemplified by F-127 (polyoxyethylene(196) polyoxypropylene(67) glycol)] and Unilube™ [product of Nippon Oil & Fats Co., Ltd., as exemplified by 70DP-950B (polyoxyethylene(200) polyoxypropylene(70) glycol)].

The polyoxyethylene hydrogenated castor oil is a nonionic surfactant prepared by adding hydrogen to castor oil to form a hydrogenated oil, which is subjected to addition polymerization of ethylene oxide and commercially available products are those in which the average number of moles of the added ethylene oxide is 10, 40, 50 or 60.

Examples of the polyoxyethylene hydrogenated castor oil to be used in the invention include Nikkol™ [product of Nikko Chemicals K.K. as exemplified by HCO-10 (polyoxyethylene hydrogenated castor oil 10, with 10 moles added on average), HCO-40, HCO-50 or HCO-60], and Uniox™ (product of Nippon Fat & Oils Co., Ltd. as exemplified by HC-10, HC-40, HC-50 or HC-60). The higher the average number of moles of ethylene oxide to be added, the more preferred, with 60 being particularly preferred.

Emulsifiers that assure good stability in emulsification and satisfactory shaping upon solidification and which hence are preferred are sucrose fatty acids used alone, polyoxyethylene hydrogenated castor oil used alone, or the combination of polyoxypolypropylene glycols and glycerol, with the sucrose fatty acids or polyoxyethylene hydrogenated castor oil used alone being more preferred. When emulsifiers are to be used in combination, the proportions at which they are mixed are in no way limited.

The content of the emulsifier in the ulinastatin-containing suppository of the invention should be such that stable emulsification will be assured during manufacture and for that matter it is preferably 0.05-10 wt %, more preferably 0.05-5 wt %, of the total quantity of the ulinastatin-containing suppository of the invention. If emulsifiers are to be used in combination, their content is preferably 0.1-7 wt %.

The more emulsifier that is used, the higher the stability in emulsification, which hence suits manufacturing purposes; however, if too much emulsifier is employed, air bubbles are prone to occur during the preparation of the suppository composition and the solidified suppository composition will involve air entrapment and shrinkage to cause nonuniformity in properties and lower hardness. The excessive emulsifier may also be a problem with the safety of pharmaceuticals. Further, depending on the type of the emulsifier and its combination with the medicinal component, the excessive emulsifier will reduce the releasability of the drug, thereby deteriorating the performance of the suppository; in addition, if the emulsifier is adsorbed on the medicinal component, particularly the protein, in aqueous solution, the drug activity may decrease.

The most preferred content of the emulsifier which is a minimum level that will not affect the pharmacological activity of ulinastatin, that allows good release and that ensures stable emulsification during manufacture is 0.5-5 wt %, more preferably 1.0-2.5 wt %, if the emulsifier is a sucrose fatty acid ester. With Unilube 70DP-950B, the preferred content is 1-10 wt %, more preferably 2-3 wt %. With Pluronic F-127, the preferred content is 0.2-1 wt %, more preferably 0.2-0.3 wt %. With conc. glycerin, the preferred content is 1-4 wt %. With polyoxyethylene hydrogenated castor oil, the preferred content is 0.05-4.3 wt %, more preferably 0.1—less than 1 wt %. Conc. glycerin is preferably used in combination with other emulsifiers. In the case of polyoxyethylene hydrogenated castor oil, products in which the average number of moles of added ethylene oxide is at least 50, particularly 60, are preferred since when present in 0.05—less than 1 wt %, particularly 0.05-0.5 wt %, they do not reduce the activity of ulinastatin in aqueous solution and yet ensure its good release.

The stabilizer to be used in the present invention is selected from among amino acids or salts thereof, proteins and sugars. Specifically, amino acids include basic amino acids such as arginine and lysine, as well as acidic amino acids such as glutamic acid and aspartic acid; proteins include gelatin and albumin; and sugars include disaccharides such as sucrose and maltose, as well as sugar alcohols such as mannitol and sorbitol. Amino acid salts are available in two salt types, one with inorganic acids and the other with organic acids, and either will do if they can be used as pharmaceuticals. Preferred examples of such salts include one with hydrochloride, sulfate, citrate, etc., with hydrochloride being more preferred. Stabilizers may be used either alone or in combination with themselves. When two or more stabilizers are to be combined, they may be mixed at any proportions.

In order to ensure good storage stability, amino acids or salts thereof and proteins are preferably used as stabilizers. Arginine is a preferred amino acid and if arginine is to be used in salt form, a hydrochloride is preferably used. Gelatin is a preferred protein. The content of the stabilizer in the suppository of the invention is preferably 0.05-5 wt %, more preferably 0.1-3 wt %, of the total quantity of the ulinastatin-containing suppository of the invention. A minimum quantity of the stabilizers that can ensure the long-term storage stability of ulinastatin is most preferably at 0.2-2 wt %.

Examples of the combination of the emulsifier and the stabilizer that are to be added to the suppository of the invention include the following: a sucrose fatty acid ester and an amino acid or a salt thereof; a sucrose fatty acid ester and a protein; a sucrose fatty acid ester and a sugar; glycerol and an amino acid or a salt thereof; glycerol and a protein; glycerol and a sugar; a polyoxyethylene polyoxypropylene glycol and an amino acid or a salt thereof; a polyoxyethylene polyoxypropylene glycol and a protein; a polyoxyethylene polyoxypropylene glycol and a sugar; glycerol or a polyoxyethylene polyoxypropylene glycol and an amino acid or a salt thereof; glycerol or a polyoxyethylene polyoxypropylene glycol and a protein; glycerol or a polyoxyethylene polyoxypropylene glycol and a sugar; glycerol or a polyoxyethylene polyoxypropylene glycol and an amino acid or a salt thereof or a protein; polyoxyethylene hydrogenated castor oil and an amino acid or a salt thereof; polyoxyethylene hydrogenated castor oil and a protein; and polyoxyethylene hydrogenated castor oil and a sugar.

The preferred combinations are as follows: a sucrose fatty acid ester and an amino acid or a salt thereof; glycerol or a polyoxyethylene polyoxypropylene glycol and a protein; glycerol or a polyoxyethylene polyoxypropylene glycol and an amino acid or a salt thereof or a protein; polyoxyethylene hydrogenated castor oil and an amino acid or a salt thereof. Specifically, the combination of a sucrose fatty acid ester and arginine or a salt thereof, the combination of glycerol or a polyoxyethylene polyoxypropylene glycol and gelatin, the combination of glycerol or a polyoxyethylene polyoxypropylene glycol and gelatin or arginine or a salt thereof, and the combination of polyoxyethylene hydrogenated castor oil and arginine or a salt thereof are preferably used since they ensure satisfactory characteristics such as good stability during storage, good stability in emulsification during manufacture and good shaping upon solidification. A more preferred combination is that of a sucrose fatty acid ester and arginine hydrochloride or that of polyoxyethylene hydrogenated castor oil and arginine hydrochloride.

The ulinastatin in the suppository of the invention is not in a simple aqueous solution but differs from it in that the aqueous phase (water droplets) are dispersed in the oily base as accompanied by the emulsifier. Therefore, conventional stabilizers are not necessarily useful as one for the suppository in an emulsified system.

Considering this point, as well as the use of ulinastatin as a medication in suppository, the characteristics as a pharmaceutical product and its indications would render it important to combine additives in an optimal way for use in suppositories.

Depending on the emulsifier to be used, the pH of the aqueous phase varies but the pH may be adjusted to lie within a stable range for ulinastatin such that ulinastatin is stabilized irrespective of the type of the emulsifier. Further, the ulinastatin can be rendered more stable by adding the aforementioned additives. If desired, the ulinastatin can be stabilized by merely adding stabilizers without pH adjustment.

The pH range desirable for the stabilization of ulinastatin is not more than 7, with 3.5–7 being more preferable and 5–6 being particularly preferred.

Exemplary pH adjusting agents that can be added are hydrochloric acid, acetic acid, citric acid, lactic acid and any other acids that can be used in pharmaceutical products. Alternatively, buffer solutions comprising these acids in combination with other salts may be added. If desired, both acids and buffer solutions may be used as pH adjusting agents.

Depending on the need, the suppository of the invention may have appropriate amounts of isotonic agents such as sodium chloride and potassium chloride, antiseptics typified by paraoxybenzoic acid esters such as methyl paraoxybenzoate and propyl paraoxybenzoate, antioxidants, coloring agents, fragrances, anti-fissuring agents, additives for adjusting hardness and feel, or any other additives that can customarily be added.

The ulinastatin-containing suppository of the invention is produced by first preparing an aqueous solution of ulinastatin in accordance with the method already described above, then adding to it the respective additives already described above.

Stated more specifically, an oily base and an emulsifier are weighed, heated at 50°–80° C. to melt and mixed uniformly to provide an oil-phase component, which is then held at a temperature suitable for emulsification. If necessary, a weighed antiseptic or other oleophilic additives may be added to the oil-phase component. In a separate step, an aqueous-phase component is prepared by first diluting an aqueous solution of ulinastatin with purified water to the necessary concentration, adding a stabilizer, optionally heating the mixture to make a uniform solution, which is thereafter held at a temperature suitable for emulsification. If necessary, an isotonic agent and other water-soluble additives may be added.

The thus prepared oil-phase and aqueous-phase components are charged into an emulsifying vessel held at a temperature suitable for emulsification, emulsified with a homomixer and applied in appropriate amounts into suppository containers. The contents are cooled to solidify, yielding uniform suppositories. Depending on their physicochemical property (solubility), the additives mentioned above may be added to an appropriately selected oil-phase or aqueous-phase component. The diluting purified water is of such a grade that it is generally suitable for use in the manufacture of pharmaceutical products.

The temperature suitable for emulsification is preferably 35°–60° C., more preferably 35°–45° C.

The appropriate amount of the aqueous solution of ulinastatin to be contained in the suppository of the invention is 0.5–30 wt %, preferably 3–25 wt %, more preferably 10–15 wt %, of the total quantity of the suppository.

In the process of the invention, the concentration of ulinastatin in aqueous solution can be adjusted by either diluting or concentrating the solution to a desired level in accordance with the need. It is also possible to provide a desired setting for the weight of each suppository by changing the filling container. Additionally, the content of ulinastatin in each suppository can be set at a desired level by adjusting a relevant factor such as the concentration of ulinastatin in aqueous solution, the ratio at which the aqueous solution of ulinastatin is mixed with the oleaginous base or the weight setting of each suppository.

For example, the case where 12 mL of the aqueous solution of ulinastatin diluted with purified water to 49,020 units/mL is emulsified in the oleaginous base with the use of an emulsifier to give a total weight of 100 g; if each suppository container is filled with 1.7 g of the emulsion, and after solidifying one can produce ulinastatin-containing suppositories each containing 10,000 units of ulinastatin.

Also consider the case where 20 mL of the aqueous solution of ulinastatin diluted with purified water to 50,000 units/mL is emulsified in the oleaginous base with the use of an emulsifier to give a total weight of 100 g; if each suppository container is filled with 3.0 g of the emulsion, and after solidifying one can produce ulinastatin-containing suppositories each containing 30,000 units of ulinastatin.

The process for producing the ulinastatin of the invention embraces all possible combinations of such factors as the concentration of ulinastatin in aqueous solution applicable to the manufacture of said suppository, the weight of each filling vessel and the ratio at which the aqueous solution of ulinastatin is mixed with the oleaginous base.

The suppository of the invention may be administered either rectally or into the vagina and a suitable route should be selected as appropriate for the indicated disease or the object of use as to whether a systemic or local action is desired. If topical administration is necessary as in threatened abortion, administration into the vagina is required.

The dose of the suppository should be varied as appropriate for such factors as the frequency of administration per day, the content of ulinastatin in a single suppository and the severity of the disease to be treated.

The content in the suppository of the invention is variable as described above. Generally, the content of ulinastatin ranges from one thousand to a hundred thousand units per suppository. To attain the desired pharmacological effect, the content of ulinastatin ranges preferably from one thousand to fifty thousand units per suppository and it is particularly preferred to have one thousand to twenty thousand units of ulinastatin contained per suppository.

On the pages that follow, examples of the present invention and experimental cases are set forth in order to describe the invention in greater detail.

Pharmaceutical formulations for the invention will now be set forth specifically as examples but the present invention is in no way limited by these examples.

EXAMPLE 1

Hard fat (Witepsol W35™ of Hüls AG; 167.4 g), polyoxyethylene[196] polyoxypropylene[67] glycol (Pluronic F-127™ of Asahi Denka Freund Sangyo K.K.; 0.6 g), propyl paraoxybenzoate (0.2 g) and methyl paraoxybenzoate (0.2 g) were weighed, melted at 50°–60° C. and processed to prepare a uniform oil-phase component, which was held at 35°–45° C.

In the next step, an aqueous solution of ulinastatin (ulinastatin: 4,900 units/mL) was prepared to have a sodium chloride concentration of 9 mg/mL; to 24 mL of the solution, there were added gelatin (2.4 g), conc. glycerin (4.8 g) and arginine hydrochloride (0.4 g) and the mixture was heated to prepare a uniform aqueous-phase component, which was held at 35°–45° C.

The thus prepared oil-phase and aqueous-phase components were mixed at 35°–45° C. to give a total amount of 200 g. The mixture was emulsified with a homomixer, filled into suppository containers such that each contained a 1.7 g portion. The contents were left to cool and solidify, yielding suppositories containing ulinastatin in a uniform amount.

EXAMPLE 2

Hard fat (Witepsol W35™ of Hüls AG; 167.4 g), polyoxyethylene[196] polyoxypropylene[67] glycol (Pluronic F-127™ of Asahi Denka Freund Sangyo K.K.; 0.6 g), propyl paraoxybenzoate (0.2 g) and methyl paraoxybenzoate (0.2 g) were weighed, melted at 50°–60° C. and processed to prepare a uniform oil-phase component, which was held at 35°–45° C.

In the next step, an aqueous solution of ulinastatin (ulinastatin: 98,040 units/mL) was prepared to have a sodium chloride concentration of 9 mg/mL; to 24 mL of the solution, there were added gelatin (2.4 g), conc. glycerin (4.8 g) and arginine hydrochloride (0.4 g) and the mixture was heated to prepare a uniform aqueous-phase component, which was held at 35°–45° C.

The thus prepared oil-phase and aqueous-phase components were mixed at 35°–45° C. to give a total amount of 200 g. The mixture was emulsified with a homomixer, filled into suppository containers such that each contained a 1.7 g portion. The contents were left to cool and solidify, yielding suppositories containing ulinastatin in a uniform amount.

EXAMPLE 3

Hard fat (Witepsol W35™ of Hüls AG; 162.4 g), polyoxyethylene[200] polyoxypropylene[70] glycol (Unilube 70DP-950B™ of Nippon Oil & Fats Co., Ltd.; 6.0 g), propyl paraoxybenzoate (0.2 g) and methyl paraoxybenzoate (0.2 g) were weighed, melted at 50°–60° C. and processed to prepare a uniform oil-phase component, which was held at 35°–45° C.

In the next step, an aqueous solution of ulinastatin (ulinastatin: 49,020 units/mL) was prepared to have a sodium chloride concentration of 9 mg/mL; to 24 mL of the solution, there were added gelatin (2.4 g) and conc. glycerin (4.8 g) and the mixture was heated to prepare a uniform aqueous-phase component, which was held at 35°14 45° C.

The thus prepared oil-phase and aqueous-phase components were mixed at 35°–45° C. to give a total amount of 200 g. The mixture was emulsified with a homomixer, filled into suppository containers such that each contained a 1.7 g portion. The contents were left to cool and solidify, yielding suppositories containing ulinastatin in a uniform amount.

EXAMPLE 4

Hard fat (Witepsol W35™ of Hüls AG; 2760.8 g), polyoxyethylene[200] polyoxypropylene[70] glycol (Unilube 70DP-950™ of Nippon Oil & Fats Co., Ltd.; 102 g), propyl paraoxybenzoate (3.4 g) and methyl paraoxybenzoate (3.4 g) were weighed, melted at 50°–75° C. and processed to prepare a uniform oil-phase component, which was held at 35°–45° C.

In the next step, an aqueous solution of ulinastatin (ulinastatin: 4,900 units/mL) was prepared to have a sodium chloride concentration of 9 mg/mL; to 408 mL of the solution, there were added gelatin (40.8 g) and conc. glycerin (81.6 g) and the mixture was heated to prepare a uniform aqueous-phase component, which was held at 35°–45° C.

The thus prepared oil-phase and aqueous-phase components were mixed at 35°–45° C. to give a total amount of 3,400 g. The mixture was emulsified with a homomixer, filled into suppository containers such that each contained a 1.7 g portion. The contents were left to cool and solidify, yielding suppositories containing ulinastatin in a uniform amount.

EXAMPLE 5

Hard fat (Witepsol W35™ of Hüls AG; 173.6 g), a sucrose fatty acid ester (Ryoto Sugar Ester S-170™ of Mitsubishi Kagaku Foods Co., Ltd.; 2.0 g), propyl paraoxybenzoate (0.2 g) and methyl paraoxybenzoate (0.2 g) were weighed, melted at 50°–60° C. and processed to prepare a uniform oil-phase component, which was held at 35°–45° C.

In the next step, an aqueous solution of ulinastatin (ulinastatin: 49,020 units/mL) was prepared to have a sodium chloride concentration of 9 mg/mL; 24 mL of the solution was mixed with the oil-phase component at 35°14 45° C. to give a total amount of 200 g. The mixture was emulsified with a homomixer, filled into suppository containers such that each contained a 1.7 g portion. The contents were left to cool and solidify, yielding suppositories containing ulinastatin in a uniform amount.

EXAMPLE 6

Hard fat (Witepsol W35™ of Hüls AG; 173.2 g), a sucrose fatty acid ester (Ryoto Sugar Ester S-170™ of Mitsubishi Kagaku Foods Co., Ltd.; 2.0 g), propyl paraoxybenzoate (0.2 g) and methyl paraoxybenzoate (0.2 g) were weighed, melted at 50°–60° C. and processed to prepare a uniform oil-phase component, which was held at 35°–45° C.

In the next step, an aqueous solution of ulinastatin (ulinastatin: 4,900 units/mL) was prepared to have a sodium chloride concentration of 9 mg/mL; to 24 mL of the solution, there was added arginine hydrochloride (0.4 g) to prepare an aqueous-phase component, which was held at 35°–45° C.

The thus prepared oil-phase and aqueous-phase components were mixed at 35°–45° C. to give a total amount of 200 g. The mixture was emulsified with a homomixer, filled into suppository containers such that each contained a 1.7 g portion. The contents were left to cool and solidify, yielding suppositories containing ulinastatin in a uniform amount.

EXAMPLE 7

Hard fat (Witepsol W35™ of Hüls AG; 173.2 g), a sucrose fatty acid ester (Ryoto Sugar Ester S-170™ of Mitsubishi Kagaku Foods Co., Ltd.; 2.0 g), propyl paraoxybenzoate (0.2 g) and methyl paraoxybenzoate (0.2 g) were weighed, melted at 50°–60° C. and processed to prepare a uniform oil-phase component, which was held at 35°–45° C.

In the next step, an aqueous solution of ulinastatin (ulinastatin: 98,040 units/mL) was prepared to have a sodium chloride concentration of 9 mg/mL; to 24 mL of the solution, there was added arginine hydrochloride (0.4 g) to prepare an aqueous-phase component, which was held at 35°–45° C.

The thus prepared oil-phase and aqueous-phase components were mixed at 35°–45° C. to give a total amount of 200 g. The mixture was emulsified with a homomixer, filled into suppository containers such that each contained a 1.7 g portion. The contents were left to cool and solidify, yielding suppositories containing ulinastatin in a uniform amount.

EXAMPLE 8

Hard fat (Witepsol W35™ of Hüls AG; 175.4 g), polyoxyethylene hydrogenated castor oil (HCO-60™ of Nikko Chemicals K.K.; 0.2 g), propyl paraoxybenzoate (0.06 g) and methyl paraoxybenzoate (0.36 g) were weighed, melted at 50°–60° C. and processed to prepare a uniform oil-phase component, which was held at 35°–45° C.

In the next step, an aqueous solution of ulinastatin (ulinastatin: 4,900 units/mL) was prepared to have a sodium chloride concentration of 9 mg/mL; to 24 mL of the solution, there was added arginine hydrochloride (0.4 g) and after adjustment with 0.05N HCl to provide a pH of 5.6, the resulting aqueous-phase component was held at 35°–45° C.

The thus prepared oil-phase and aqueous-phase components were mixed at 35°–45° C. to give a total amount of 200 g. The mixture was emulsified with a homomixer, filled into suppository containers such that each contained a 1.7 g portion. The contents were left to cool and solidify, yielding suppositories containing ulinastatin in a uniform amount.

EXAMPLE 9

Hard fat (Witepsol W35™ of Hüls AG; 175.4 g), polyoxyethylene hydrogenated castor oil (HCO-60™ of Nikko Chemicals K.K.; 0.2 g), propyl paraoxybenzoate (0.06 g) and methyl paraoxybenzoate (0.36 g) were weighed, melted at 50°–60° C. and processed to prepare a uniform oil-phase component, which was held at 35°–45° C.

In the next step, an aqueous solution of ulinastatin (ulinastatin: 98,040 units/mL) was prepared to have a sodium chloride concentration of 9 mg/mL; to 24 mL of the solution, there was added arginine hydrochloride (0.4 g) and after adjustment with 0.05N HCl to provide a pH of 5.6, the resulting aqueous-phase component was held at 35°–45° C.

The thus prepared oil-phase and aqueous-phase components were mixed at 35°–45° C. to give a total amount of 200 g. The mixture was emulsified with a homomixer, filled into suppository containers such that each contained a 1.7 g portion. The contents were left to cool and solidify, yielding suppositories containing ulinastatin in a uniform amount.

Control

A solution having sodium chloride (9 mg) and gelatin (5 mg) added to ulinastatin (51,500 units) was freeze-dried to a powder form. To an adequate amount (equivalent to $1.2 \times 10^6$ units) of the powder, there was added hard fat (trade name: Witepsol W35™ of Hüls AG) that had been melted at 50°–60° C., thereby giving a total quantity of 204 g. The mixture was dispersed with a homomixer and filled into suppository containers such that each contained a 1.7 g portion. The contents were left to cool and solidify, yielding uniform suppositories.

Exiperimental Case

The suppositories prepared in Examples 1–8 and in the Control were stored at 30° C. for 3 months and their stability during long-term storage was evaluated by measuring the content of the ulinastatin aggregates. The results are shown in Table 1. The suppositories prepared in Examples 8 and 9 were also stored at 4° C. for six months and the results are shown in Table 2.

Analyses were carried out by gel filtration on a TSK-gel TM G3000 (Tosoh Corp.) column and the percent content of the aggregates in each sample was calculated.

Direct contact between the oleaginous base and ulinastatin causes not only a change in the higher-order structure of ulinastatin but also its aggregation. Since the progress of aggregation results in a lower titer, the percent content of ulinastatin aggregates in the oily base is a good index for the stability of the composition of the present invention.

TABLE 1

| | Percent Content of Aggregate | | |
|---|---|---|---|
| | At start | 2 months | 3 months |
| Control | 0.0 | 3.5 | 4.7 |
| Example 1 | 0.0 | 0.0 | 0.0 |
| Example 2 | 0.0 | 0.0 | 0.0 |
| Example 3 | 0.0 | 0.0 | 0.0 |
| Example 4 | 0.0 | 0.0 | 0.0 |
| Example 5 | 0.0 | 2.1 | 2.2 |
| Example 6 | 0.0 | 0.0 | 0.0 |
| Example 7 | 0.0 | 0.0 | 0.0 |
| Example 8 | 0.0 | 0.0 | — |

TABLE 2

| | Percent Content of Aggregate | | |
|---|---|---|---|
| | At start | 4 months | 6 months |
| Example 8 | 0.0 | 0.0 | 0.0 |
| Example 9 | 0.0 | 0.0 | 0.0 |

As Table 1 shows, the control ulinastatin suppository had the aggregate content increased up to about 5%; on the other hand, the ulinastatin-containing suppositories of Examples 1–8 were substantially free from the increase of aggregates, indicating their excellent long-term stability. Further, as Table 2 shows, the ulinastatin-containing suppositories of Examples 8 and 9 were stable over prolonged storage in a cool place.

Thus, it was demonstrated that when an aqueous solution of ulinastatin (a trypsin inhibitor derived from human urine) supplemented with a stabilizer such as arginine hydrochloride or gelatin was emulsified in an oily base uniformly to be formulated as a suppository with the aid of a surfactant such as a sucrose fatty acid ester, glycerol, a polyoxyethylene polyoxypropylene glycol or polyoxyethylene hydrogenated castor oil, the ulinastatin in the oily base was effectively stabilized during prolonged storage.

Industrial Applicability

The thus prepared ulinastatin-containing suppository of the invention is characterized in that an aqueous solution of ulinastatin (a trypsin inhibitor derived from human urine) supplemented with a stabilizer such as arginine hydrochloride or gelatin is emulsified in an oily base uniformly with the aid of a surfactant such as a sucrose fatty acid ester, glycerol, a polyoxyethylene polypropylene glycol or polyoxyethylene hydrogenated castor oil and, hence, the ulinastatin in the oily base is assured of good stability during prolonged storage.

In addition, formulating the suppository of the invention as an emulsion eliminates the step of freeze- drying the aqueous solution of ulinastatin which has been necessary in the prior art. Namely, with the conventional formulae, the freeze-dried powder has to be dispersed in the oily base and, hence, it is difficult to achieve uniform mixing. On the other hand, the present invention facilitates the production of suppositories of uniform composition, thereby enabling the manufacture of ulinastatin-containing suppositories on an industrial scale.

Therefore, according to the suppository producing process of the invention, not only is it possible to provide a ulinastatin-containing suppository having good stability during prolonged storage but also the time required to produce the ulinastatin-containing suppository of the invention is sufficiently shortened to enable the reduction of the production cost.

We claim:

1. An ulinastatin-containing suppository composition produced by the steps comprising:

preparing an aqueous solution of ulinastatin comprising 0.05 to 5% by weight in total suppository composition of a stabilizer, uniformly emulsifying the solution in an oily base in the presence of an emulsifier of 0.05 to 10% by weight in total suppository composition, and solidifying the emulsion;

wherein said stabilizer is at least one member selected from the group consisting of basic amino acids and salts thereof, acidic amino acids and salts thereof, gelatin, albumin, disaccharides and sugar alcohols; and wherein said emulsifier is at least one member selected from the group consisting of sucrose fatty acid esters, concentrated glycerin, glycerol, polyoxyethylene polyoxypropylene glycols, and polyoxyethylene hydrogenated caster oil.

2. The ulinastatin-containing suppository composition according to claim 1, wherein said aqueous ulinastatin solution contains 0.1 to 3% by weight of arginine hydrochloride and/or gelatin, and said stabilizer-containing aqueous ulinastatin solution is emulsified in an oily base in the presence of 1.0 to 2.5% by weight of sucrose fatty acid esters or 0.05 to 0.5% by weight of polyoxyethylene hydrogenated castor oil in which the average number of moles of added ethylene oxide is 60.

3. The ulinastatin-containing suppository composition according to claim 1, wherein said oily base is a hard fat.

4. The ulinastatin-containing suppository comprising the composition according to claim 1, wherein said suppository is adapted for vaginal administration.

* * * * *

UNITED STATES PATENT AND TRADEMARK OFFICE
CERTIFICATE OF CORRECTION

PATENT NO. : 5,783,555
DATED : July 21, 1998
INVENTOR(S) : Suzuki, et al.

It is certified that error appears in the above-identified patent and that said Letters Patent is hereby corrected as shown below:

On the title page, change "4 Claims" to read --5 Claims--.

Columns 16, line 21, insert the following new claim;

A method for treating threatened premature delivery, comprising administering an effective amount of the ulinastatin-containing suppository composition according to claim 1.

Signed and Sealed this

Sixteenth Day of February, 1999

Attest:

Attesting Officer

*Acting Commissioner of Patents and Trademarks*